(12) United States Patent
Shetty et al.

(10) Patent No.: US 8,278,510 B2
(45) Date of Patent: Oct. 2, 2012

(54) CUCUMBER LINE APD147-5007GY

(75) Inventors: Nischit Shetty, Tifton, GA (US); Greg Tolla, Woodland, GA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 717 days.

(21) Appl. No.: 12/197,824

(22) Filed: Aug. 25, 2008

(65) Prior Publication Data

US 2009/0064355 A1 Mar. 5, 2009

Related U.S. Application Data

(60) Provisional application No. 60/969,141, filed on Aug. 30, 2007, provisional application No. 61/012,489, filed on Dec. 10, 2007.

(51) Int. Cl.
*A01H 1/00* (2006.01)
*A01H 5/10* (2006.01)
*A01H 5/00* (2006.01)
*C12N 15/82* (2006.01)

(52) U.S. Cl. ......... 800/307; 435/410; 435/6.1; 800/260; 800/278

(58) Field of Classification Search ........................ None
See application file for complete search history.

(56) References Cited

U.S. PATENT DOCUMENTS

| | | | |
|---|---|---|---|
| 5,492,827 A | 2/1996 | Dirks | 435/999.999 |
| 2008/0229440 A1 | 9/2008 | Shetty | 800/307 |
| 2009/0210964 A1 | 8/2009 | Shetty | |

OTHER PUBLICATIONS

U.S. PVP Application No. for *Cucumis sativaus* L. Variety APD147-5002GY, dated Nov. 9, 2007.
Request for Information under 37 CFR § 1.105 regarding U.S. Appl. No. 12/014,643, dated Jun. 12, 2009.
Response to Request for Information under 37 CFR § 1.105 regarding U.S. Appl. No. 12/014,643, dated Oct. 19, 2009.
Request for Information under 37 CFR § 1.105 regarding U.S. Appl. No. 12/014,643, dated Oct. 22, 2010.
Response to Request for Information under 37 CFR § 1.105 regarding U.S. Appl. No. 12/014,643, dated Jan. 13, 2011.
U.S. Application for Plant Variety Protection for Cucumber Variety (*Cucumis sativus* L.) APD147-5007Gy, filed Nov. 13, 2007.
Sarreb et al., "Comparison of triploid and diploid cucumber in long-term liquid cultures," *Plant Cell, Tissue and Organ Culture*, 71:231-235, 2002.

*Primary Examiner* — Brent T Page
(74) *Attorney, Agent, or Firm* — SNR Denton US LLP; Alissa Eagle Esq.

(57) ABSTRACT

The invention provides seed and plants of the cucumber line designated APD147-5007Gy. The invention thus relates to the plants, seeds and tissue cultures of cucumber line APD147-5007Gy, and to methods for producing a cucumber plant produced by crossing a plant of cucumber line APD147-5007Gy with itself or with another cucumber plant, such as a plant of another line. The invention further relates to seeds and plants produced by such crossing. The invention further relates to parts of a plant of cucumber line APD147-5007Gy, including the fruit and gametes of such plants.

23 Claims, No Drawings

CUCUMBER LINE APD147-5007GY

This application claims the priority of U.S. Provisional Appl. Ser. No. 60/969,141 filed Aug. 30, 2007, and U.S. Provisional Appl. Ser. No. 61/012,489 filed Dec. 10, 2007, the entire disclosure of which is incorporated herein by reference.

BACKGROUND OF THE INVENTION

1. Field of the Invention

The present invention relates to the field of plant breeding and, more specifically, to the development of cucumber line APD147-5007Gy.

2. Description of Related Art

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is the cucumber. Cucumber (*Cucumis sativus* L.) is naturally a diploid (2n=14) outcrossing species originating in Asia or Africa, although haploid, doubled-haploid (U.S. Pat. No. 5,492,827), and triploid (Sarreb et al., 2002) types have been developed. Humans have cultivated cucumbers for several thousand years. The cucumber has large leaves that form a canopy over the fruit. The vine is grown on the ground or on trellises. The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as developing and large seeds are not palatable.

Until the 1960s cucumbers were normally monoecious, e.g., having separate male and female flowers on the same plant. Perfect flowers are uncommon in cucumbers. Staminate flowers are typically single and/or in clusters. Pistillate flowers may be solitary or in clusters and are borne on stout peduncles. Gynoecious cucumber plants have now been identified in which flowers are exclusively pistillate. These plants are generally higher yielding, due at least in part to the presence of higher numbers of female flowers. However, growth of gynoecious hybrid plants in the field has historically required the addition of plants of a monoecious line or variety (~10-15%) to ensure availability of pollen and setting of fruit with seed. Honey bees are the most commonly used insects to pollinate cucumbers in the open field.

Cucumber plants that set fruit parthenocarpically (without pollination and fertilization) have more recently been available. These plants produce seedless fruit unless pollinated. Growth of parthenocarpic varieties is beneficial in that setting of fruit on these cultivars does not produce an inhibiting effect on plant growth, unlike the case of fertilized, seeded fruit. The seedless varieties are usually higher yielding and of higher quality due to the lack of seeds. However, growth of these plants requires isolation from seeded cucumbers to avoid pollination and subsequent seeded fruit.

Most of the cucumbers currently used which are processed to pickles and pickle products in the United States are seeded hybrid varieties. Hybrid varieties offer the advantages of easy combination of dominant and recessive traits, such as disease resistance, from a set of inbred parents, as well as careful control of parentage. The production of $F_1$ hybrid cucumber seeds from a pollen parent bearing only male flowers has been reported (U.S. Pat. No. 4,822,949).

Many different cucumber cultivars have been produced, and cucumber breeding efforts have been underway in many parts of the world (see, e.g. U.S. Pat. No. 6,765,130). Some breeding objectives include varying the color, texture and flavor of the fruit. Minimizing the occurrence of bitterness in cucumbers is one such example. Other objectives include optimizing flesh thickness, solid content (% dry matter), and sugar content. Also, breeding programs have focused on developing plants with earlier fruit maturity, more restricted vine growth, improved disease resistance or tolerance, and improved adaptability to environmental conditions.

Advances in biotechnology have resulted in genetically engineered cucumber plants with improved. For example, cucumbers resistant to CMV have been developed by expression of CMV protein coat genes (see e.g., U.S. Pat. No. 6,342,655, U.S. Pat. No. 6,127,601, U.S. Pat. No. 5,623,066, U.S. Pat. No. 5,349,128). Transgenic plants exhibiting, for example, other viral resistance traits or high levels of superoxide dismutase have also been reported (U.S. Pat. No. 6,015, 942; U.S. Pat. No. 6,084,152).

While breeding efforts to date have provided a number of useful cucumber lines with beneficial traits, there remains a great need in the art for new lines with further improved traits. Such plants would benefit farmers and consumers alike by improving crop yields and/or quality.

SUMMARY OF THE INVENTION

In one aspect, the present invention provides a cucumber plant of the line designated APD147-5007Gy. Also provided are cucumber plants having all the physiological and morphological characteristics of the cucumber line designated APD147-5007Gy. Parts of the cucumber plant of the present invention are also provided, for example, including pollen, an ovule, a seed, a fruit, and a cell of the plant.

The invention also concerns the seed of cucumber line APD147-5007Gy. The cucumber seed of the invention may be provided as an essentially homogeneous population of cucumber seed of the line designated APD147-5007Gy. Essentially homogeneous populations of seed are generally free from substantial numbers of other seed. Therefore, seed of line APD147-5007Gy may be defined as forming at least about 97% of the total seed, including at least about 98%, 99% or more of the seed. The population of cucumber seed may be particularly defined as being essentially free from hybrid seed. The seed population may be separately grown to provide an essentially homogeneous population of cucumber plants designated APD147-5007Gy.

In another aspect of the invention, a plant of cucumber line APD147-5007Gy comprising an added heritable trait is provided. The heritable trait may comprise a genetic locus that is, for example, a dominant or recessive allele. In one embodiment of the invention, a plant of cucumber line APD147-5007Gy is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a cucumber plant of line APD147-5007Gy is provided. The tissue culture will preferably be capable of regenerating cucumber plants capable of expressing all of the physiological and morphological characteristics of the line, and of regenerating plants having substantially the same genotype as other plants of the line. Examples of some of the physiological and morphological characteristics of the line APD147-5007Gy include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides cucumber plants regenerated from a tissue culture of the invention, the plants having all the physiological and morphological characteristics of line APD147-5007Gy.

In yet another aspect of the invention, processes are provided for producing cucumber seeds, plants and fruit, which processes generally comprise crossing a first parent cucumber plant with a second parent cucumber plant, wherein at least one of the first or second parent cucumber plants is a plant of the line designated APD147-5007Gy. These processes may be further exemplified as processes for preparing hybrid cucumber seed or plants, wherein a first cucumber plant is crossed with a second cucumber plant of a different, distinct line to provide a hybrid that has, as one of its parents, the cucumber plant line APD147-5007Gy. In these processes, crossing will result in the production of seed. The seed production occurs regardless of whether the seed is collected or not.

In one embodiment of the invention, the first step in "crossing" comprises planting seeds of a first and second parent cucumber plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent cucumber plants into plants that bear flowers. A third step may comprise preventing self-pollination of the plants, such as by emasculating the male portions of flowers, (i.e., treating or manipulating the flowers to produce an emasculated parent cucumber plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent cucumber plants. Yet another step comprises harvesting the seeds from at least one of the parent cucumber plants. The harvested seed can be grown to produce a cucumber plant or hybrid cucumber plant.

The present invention also provides the cucumber seeds and plants produced by a process that comprises crossing a first parent cucumber plant with a second parent cucumber plant, wherein at least one of the first or second parent cucumber plants is a plant of the line designated APD147-5007Gy. In one embodiment of the invention, cucumber seed and plants produced by the process are first generation ($F_1$) hybrid cucumber seed and plants produced by crossing a plant in accordance with the invention with another, distinct plant. The present invention further contemplates plant parts of such an $F_1$ hybrid cucumber plant, and methods of use thereof. Therefore, certain exemplary embodiments of the invention provide an $F_1$ hybrid cucumber plant and seed thereof.

In still yet another aspect, the present invention provides a method of producing a plant derived from line APD147-5007Gy, the method comprising the steps of: (a) preparing a progeny plant derived from line APD147-5007Gy, wherein said preparing comprises crossing a plant of the line APD147-5007Gy with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line APD147-5007Gy. The plant derived from line APD147-5007Gy may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line APD147-5007Gy is obtained which possesses some of the desirable traits of the line as well as potentially other selected traits.

In certain embodiments, the present invention provides a method of producing cucumbers comprising: (a) obtaining a plant of cucumber line APD147-5007Gy, wherein the plant has been cultivated to maturity, and (b) collecting cucumbers from the plant.

In still yet another aspect of the invention, the genetic complement of the cucumber plant line designated APD147-5007Gy is provided. The phrase "genetic complement" is used to refer to the aggregate of nucleotide sequences, the expression of which sequences defines the phenotype of, in the present case, a cucumber plant, or a cell or tissue of that plant. A genetic complement thus represents the genetic makeup of a cell, tissue or plant, and a hybrid genetic complement represents the genetic make up of a hybrid cell, tissue or plant. The invention thus provides cucumber plant cells that have a genetic complement in accordance with the cucumber plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line APD147-5007Gy could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by cucumber plant cells, tissues, plants, and seeds, formed by the combination of a haploid genetic complement of a cucumber plant of the invention with a haploid genetic complement of a second cucumber plant, preferably, another, distinct cucumber plant. In another aspect, the present invention provides a cucumber plant regenerated from a tissue culture that comprises a hybrid genetic complement of this invention.

In still yet another aspect, the invention provides a plant of an inbred cucumber line that exhibits a combination of traits comprising resistance to Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Downy mildew (*Pseudopernospora cubensis*), Powdery Mildew (*Sphaerotheca fuliginea*) and Cucumber Mosaic Virus. Cucumber line APD147-5007Gy also produces fruit with the shape, color, and spines to a typical seeded American pickling cucumber, can reproduce parthenocarpically, and provides an excellent pollen parent line and seed parent line in crosses for producing first generation (F1) hybrid cucumbers. In certain embodiments, the combination of traits may be defined as controlled by genetic means for the expression of the combination of traits found in cucumber line APD147-5007Gy.

In still yet another aspect, the invention provides a method of determining the genotype of a plant of cucumber line APD147-5007Gy comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of cucumber line APD147-5007Gy. This line shows uniformity and stability within the limits of environmental influence for the traits described hereinafter. Cucumber line APD147-5007Gy provides sufficient seed yield. By crossing with a distinct second plant, uniform F1 hybrid progeny can be obtained.

Line APD147-5007Gy exhibits a number of improved traits including resistance to Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Downy mildew (*Pseudopernospora cubensis*), Powdery Mildew (*Sphaerotheca fuliginea*) and Cucumber Mosaic Virus. Cucumber line APD147-5007Gy also produces fruit with the shape, color, and spines to a typical seeded American pickling cucumber, can reproduce parthenocarpically, and provides an excellent pollen parent line and seed parent line in crosses for producing first generation (F1) hybrid cucumbers. The development of the line can be summarized as follows.

A. Ori2 in and Breeding History of Cucumber Line APD147-5007Gy

Inbred cucumber line ADP147-5007Gy was developed from an initial single cross of Seminis Pot No. 12530× Seminis Pot No. 12533 (Seminis Vegetable Seeds Greenhouse; Tifton, Ga.). Pot No. 12530 was an inbred pickling cucumber line with good fruit quality, fruit color, fruit shape, resistance to Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Powdery Mildew (*Sphaerotheca fuliginea*) and Cucumber Mosaic Virus and good adaptability to different growing conditions in North America and Mexico. Pot No. 12533 was a parthenocarpic line from Europe with good adaptability in Europe.

After this initial cross was made, progeny were tested for parthenocarpy, gynoecy, Anthracnose, Angular leaf spot, Scab and Cucumber Mosaic Virus resistance, plant growth habit and fruit quality. After the first cross progeny were self or sib-pollinated for inbred advancement in the field during the spring of 1996. Seeds of the selection were planted in plot T96S-24001 during the summer of 1996 in the greenhouse and were selected for plant growth habit, fruit type, and parthenocarpy. Selections from plot T96S-24001 were planted during the fall of 1996 in plot T96S-24251. The plants were selfed and selections were made for fruit quality, fruit color, parthenocarpy and plant growth habit (T96F-24251DE).

Selections from plot T96F-242251BG were planted during the spring season of 1997 in plot T97S-20857, the plants were selfed and selections made for fruit quality, fruit color, parthenocarpy and plant habit. Selections from plot T97S-20857 were planted during the fall of 1997 in plot T97F-27267, and selections were made for fruit quality, fruit color and plant habit (T97F-27267A2). Selections from plot T97F-27267A2 were planted in plot T98S-31252 during the spring of 1998 in the greenhouse, plants were selfed, and selections made for fruit quality, fruit color, parthenocarpy and plant habit (T98S-31252J1). Selections from plot T98S-31252J1 were grown in the fall of 1998 in plot 36564 and were selected for fruit quality, fruit color, parthenocarpy and plant habit (T98F-36564A).

Selections from plot T98F-36564A were planted during the fall of 1999 in plot T99F-26708 for gynoecy and parthenocarpy, and selections were made for fruit quality, fruit color and plant habit (T99F-26708C1). Selections from plot 26708C1 were planted in plot T00S-21378 during the spring of 2000 in the greenhouse, were selfed, and selections were made for fruit quality, fruit color, parthenocarpy and plant habit (T00S-21378D1). Selections from plot T00S-21378D1 were planted in plot T00F-29304 during the fall of 2000 in the greenhouse, were selfed, and selections were made for fruit quality, fruit color, parthenocarpy and plant habit (T00F-29304C). Selections from plot T00F-29304C were planted in plot T01W-31908 during the winter season of 2001 in the greenhouse and were selfed, and selections were made for fruit quality, fruit color, parthenocarpy and plant habit (T01W-31908B1).

Selections from plot T0W-31908B1 were planted during the fall season of 2001 in plot T01F-38029 for gynoecy and parthenocarpy, and selections were made for fruit quality, fruit color and plant habit (T01F-38029C1). Selections from plot T01F-38029C1 were planted in plot T02W-41526 during the winter season of 2002 in the greenhouse, resistant plants were selfed, and selections were made for fruit quality, fruit color, parthenocarpy and plant habit (T02W-41526F2). Selections from plot T02W-41526F2 were planted in plot T02S-46906 during the summer of 2002 in the greenhouse, resistant plants were selfed, and selections were made for fruit quality, fruit color, parthenocarpy and plant habit (T02W-46906B). Selections from plot T02W-46906B were planted in plot T04W-52996 during the winter of 2004 in the greenhouse, plants were selfed and the line was designated as APD147-5007Gy.

B. Physiological and Morphological Characteristics of Cucumber Line APD147-5007Gy In accordance with one aspect of the present invention, there is provided a plant having the physiological and morphological characteristics of cucumber line APD147-5007Gy. A description of the physiological and morphological characteristics of cucumber line APD147-5007Gy is presented in Table 1.

TABLE 1

Physiological and Morphological Characteristics of Line APD147-5007Gy

| | CHARACTERISTIC | APD147-5007Gy |
|---|---|---|
| 1. | Type | Cucumber |
| | Predominate Usage | Pickling |
| | Predominate Culture | Outdoor |
| | Area Of Best Adaptation In USA | Most Areas |
| 2. | Maturity | |
| | Days From Seeding To Market | 48 |
| 3. | Plant | |
| | Habit | Vine |
| | Growth | Indeterminate |
| | Vigor | Weak to Medium |
| | Sex | 100% Gynoecious |
| | No. Of Female Flowers Per Node | 1-3 |
| | Flower Color | Yellow |
| 4. | Stem | |
| | Length | 259 cm |
| | Plant: Total Length Of First 15 Internodes | Short to Medium |
| | Plant: Length Of Internodes Of Side Shoots | Short |
| 5. | Leaf | Mature Blade of Third Leaf |
| | Length: Mature Blade Of Third Leaf | 265 mm |
| | Width: Mature Blade Of Third Leaf | 240 mm |
| | Size Of Blade | Small to Medium |
| | Intensity Of Green Color | Light to Medium |
| | Blistering | Absent or Very Weak |
| | Undulation Of Margin | Absent or Very Weak |
| | Length Of Terminal Lobe | Short |
| | Width Of Terminal Lobe | Narrow |
| | Ratio Length/Width Of Terminal Lobe | Equal to 1 |
| 6. | Young Fruit | |
| | Type Of Vestiture | Prickles Only |
| | Density Of Vestiture | Sparse |
| | Color Of Vestiture | White |
| | Size Of Warts | Small |
| | Parthenocarpy | Absent |
| 7. | Mature Fruit | |
| | Length | Short to Medium |
| | Fruit At Edible Maturity Diameter | 13.6 mm Small to Medium |
| | Fruit At Edible Maturity | 4.4 cm |
| | Ratio Length/Diameter | Small to Medium |
| | Core Diameter In Relation To Diameter Of Fruit | Small to Medium |
| | Fruit At Edible Maturity | 168 gm |
| | Skin Color/Mottling | Mottled or Speckled with Yellow (Delicatesse) |
| | Predominant Type Of Mottling | Small and Round |
| | Intensity Of Mottling | Weak |
| | Fruit At Edible Maturity: Yellowish Blossom End Stripes | Extended less than 1/3 of the Fruit Length |
| | Fruit At Edible Maturity: Predominant Color At Stem End | Medium Green |
| | Fruit At Edible Maturity: Predominant Color At Stem End | 137 C |
| | Fruit At Edible Maturity: Predominant Color At Blossom End | Light Green |
| | Fruit At Edible Maturity: Predominant Color At Blossom End | 145B |
| | Fruit At Edible Maturity: Fruit Neck Shape | Not Necked |
| | Fruit: Predominant Shape Of Stem End At Market Stage | Obtuse |
| | Length Of Neck | Short |
| | Fruit: Shape Of Calyx End At Market Stage | Obtuse |
| | Fruit At Edible Maturity: Fruit Tapering | Ends Blunt or Rounded |
| | Fruit At Edible Maturity: Stem End Cross Section | Circular |
| | Fruit At Edible Maturity: Medial Cross Section | Triangular |
| | Fruit At Edible Maturity: Blossom End Cross Section | Triangular |

TABLE 1-continued

Physiological and Morphological Characteristics of Line APD147-5007Gy

| CHARACTERISTIC | | APD147-5007Gy |
|---|---|---|
| | Fruit: Ground Color Of Skin At Market Stage | White |
| | Fruit: Intensity Of Ground Color Of Skin | Light to Medium |
| | Fruit At Edible Maturity: Skin Thickness | Thick |
| | Fruit At Edible Maturity: Skin Ribs | Present/Ribbed |
| | Fruit: Prominence Of Ribs | Weak to Medium |
| | Fruit: Coloration Of Ribs Compared To Ground Color | Lighter |
| | Fruit At Edible Maturity: Skin Toughness | Tough |
| | Fruit At Edible Maturity: Skin Luster | Dull |
| | Fruit At Edible Maturity: Spine Color | White |
| | Fruit At Edible Maturity: Spine Quality | Course |
| | Fruit At Edible Maturity: Spine Density | Few |
| | Fruit: Vestiture | Absent or Very Sparse to Sparse |
| | Fruit: Warts | Present |
| | Fruit At Edible Maturity: Tubercles (Warts) | Few, Obscure |
| | Fruit: Stripes (Ribs Excluded) | Present |
| | Fruit: Length Of Stripes | Short |
| | Fruit: Length Of Peduncle | Medium |
| | Fruit: Thickness Of Peduncle | Medium |
| | Fruit: Ground Color Of Skin At Physiological Ripening | White |
| | Time Of Development Of Female Flowers (80% Of Plants With At Least One Female Flower) | Medium |
| | Cotyledon: Bitterness | Absent |
| | Fruit At Edible Maturity: Flavor/Bitterness At Stem End | Absent/Bitterfree |
| | Fruit Seed At Harvest Maturity: Measurements | 1.0 cm |
| | Fruit Seed At Harvest Maturity: Measurements | 0.4 cm |
| | Fruit Seed At Harvest Maturity: Color | Cream |
| | Fruit Seed At Harvest Maturity: Color | 161D |
| | Fruit Seed At Harvest Maturity: Color Pattern | Not Striped |
| | Fruit Seed At Harvest Maturity: Surface | Smooth |
| | Fruit Seed At Harvest Maturity: Netting | Slight or None |
| | Seeds: Measurements | 95 Seeds per Fruit |
| | Seeds: Measurements | 31.1 gm per 1,000 Seeds |
| 8. | Resistance to Diseases | |
| | Resistance To Cucumber Scab (Gummosis) (*Cladosporium Cucumerinum*) | Present |
| | Resistance To Cucumis Mosaic Virus (CMV) | Present |
| | Resistance To Powdery Mildew (*Sphaerotheca Fuliginea*) | Present |
| | Resistance To Downy Mildew (*Pseudoperonospora Cubensis*) | Present |
| | Resistance To Angular Leaf Spot (*Pseudomonas Lachrymans*) | Present |
| | Resistance To Anthracnose (Race 1) (*Colletotrichum Lagenaria*) | Present |

*These are typical values. Values may vary due to environment. Other values that are substantially equivalent are within the scope of the invention.

Line APD147-5007Gy has been self-pollinated and planted for a number of generations to produce the homozygosity and phenotypic stability to make this line useful in commercial seed production. No variant traits have been observed or are expected for this line.

Cucumber line APD147-5007Gy, being substantially homozygous, can be reproduced by planting seeds of the line, growing the resulting cucumber plant under self-pollinating or sib-pollinating conditions and harvesting the resulting seeds using techniques familiar to one of skill in the art.

C. Breeding Cucumber Line APD147-5007Gy

One aspect of the current invention concerns methods for crossing the cucumber line APD147-5007Gy with itself or a second plant and the seeds and plants produced by such methods. These methods can be used for propagation of line APD147-5007Gy, or can be used to produce hybrid cucumber seeds and the plants grown therefrom. Hybrid seeds are produced by crossing line APD147-5007Gy with second cucumber parent line.

The development of new varieties using one or more starting varieties is well known in the art. In accordance with the invention, novel varieties may be created by crossing line APD147-5007Gy followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line APD147-5007Gy and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with APD147-5007Gy for the purpose of developing novel cucumber lines, it will typically be preferred to choose those plants which either themselves exhibit one or more selected desirable characteristics or which exhibit the desired characteristic(s) when in hybrid combination. Examples of desirable characteristics may include, but are not limited to, resistance to one or more viruses (e.g., cucumber mosaic virus, watermelon mosaic virus-II, cucumber necrosis virus, and cucumber vein yellowing ipomovirus, CYSDV), resistance to one or more fungal diseases (e.g., anthracnose, caused by *Colletotrichum orbiculare*, downy mildew, caused by *Pseudoperonospora cubensis*, gummy stem blight caused by *Didymella bryoniae*, and powdery mildew, caused by *Oidium* sp.), resistance one or more bacteria (e.g., angular leaf spot, caused by *Pseudomonas syringae* pv. *lachrymans*, phytopthera caused by *Phytoppthera infestans* and bacterial wilt, caused by *Erwinia tracheiphila*), and one or more insects (e.g. the seedcorn maggot, *Delia platura*, the striped cucumber beetle, *Acalymma vittatum* (Fabricius), and the spotted cucumber beetle, *Diabrotica undecimpunctata howardi* Barber). Non-limiting examples of genes that may be utilized for generating transgenic cucumber include RAR1 disease resistance proteins, as described in, for example, U.S. Pat. No. 7,098,378, the ability to tolerate high salt conditions, as described in, for example, U.S. Pat. No. 7,041,875 or U.S. Pat. No. 6,936,750; trehalose synthase for increased amounts of trehalose to increase tolerance to a variety of stresses, in particular to decreased availability of water, as described in, for example, U.S. Pat. No. 5,792,921; overexpression of phytochrome, such as for increased shade tolerance and/or darker green color, as described in, for example, U.S. Pat. No. 5,268, 526; expression of reversibly glycosylated protein (RGP) for at least altered growth rates, as described in, for example, U.S. Pat. No. 6,194,638; improved growth under low-light conditions, such as with COP1, as described in, for example, U.S. Pat. No. 7,081,363 and so forth.

Examples of desirable characteristics related to the skin of the cucumber fruit include: a certain coloring, striping, and texture. Desirable characteristics related to the flesh of the cucumber fruit include: a certain flavor, taste, texture, thickness, color, sugar content, and solids content (% dry matter). Small or nonexistent seeds is another desired trait for cucumbers. Other desirable characteristics related to the fruit include: a certain fruit size and shape. Particularly desirable traits include: high fruit yield, early maturity, improved seed germination, and high seed yield. Desirable characteristics related to the environment include: tolerance to environmental stress (e.g. frost, drought, etc.) and adaptability to a wide variety of environmental conditions (e.g. soil acidity and salinity, temperature, and moisture).

D. Performance Characteristics

As described above, line APD147-5007Gy exhibits desirable agronomic traits, including resistance to Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Downy mildew (*Pseudopernospora cubensis*), Powdery Mildew (*Sphaerotheca fuliginea*) and Cucumber Mosaic Virus. Cucumber line APD147-5007Gy also produces fruit with the shape, color, and spines to a typical seeded American pickling cucumber, can reproduce parthenocarpically, and provides an excellent pollen parent line and seed parent line in crosses for producing first generation (F1) hybrid cucumbers. These and other performance characteristics of the line were the subject of an objective analysis of the performance traits of the line relative to other lines. The results of the analysis are presented below.

E. Further Embodiments of the Invention

When the term cucumber line APD147-5007Gy is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those cucumber plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental cucumber plant which contributes the locus for the desired characteristic is termed the nonrecurrent or donor parent. This terminology refers to the fact that the nonrecurrent parent is used one time in the backcross protocol and therefore does not recur. The parental cucumber plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a cucumber plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny cucumber plants of a backcross in which APD147-5007Gy is the recurrent parent comprise (i) the desired trait from the non-recurrent parent and (ii) all of the physiological and morphological characteristics of cucumber line APD147-5007Gy as determined at the 5% significance level when grown in the same environmental conditions.

Cucumber varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the downy mildew resistance trait. For this selection process, the progeny of the initial cross are sprayed with downy mildew spores prior to the backcrossing. The spraying eliminates any plants which do not have the desired downy mildew resistance characteristic, and only those plants which have the downy mildew resistance gene are used in the subsequent backcross. This process is then repeated for all additional backcross generations.

Selection of cucumber plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of cucumber are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Cucumber Line APD147-5007Gy by Genetic Engineering

Many useful traits that can be introduced by backcrossing, as well as directly into a plant, are those which are introduced by genetic transformation techniques. Genetic transformation may therefore be used to insert a selected transgene into the cucumber line of the invention or may, alternatively, be used for the preparation of transgenes which can be introduced by backcrossing. Methods for the transformation of plants, including cucumber plants, are well known to those of skill in the art (see, e.g., Schroeder et al., 1993). Techniques which may be employed for the genetic transformation of cucumber plants include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cucumber cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for cucumber plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the cucumber lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a cucumber plant according to the invention. Non-limiting examples of particular genes and corresponding phenotypes one may choose to introduce into a cucumber plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions. $F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a cucumber variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a cucumber plant by transformation.

H. Deposit Information

A deposit of cucumber line APD147-5007Gy, disclosed above and recited in the claims, has been made with the American Type Culture Collection (ATCC), 10801 University Blvd., Manassas, Va. 20110-2209. The date of deposit was Sep. 6, 2007. The accession number for those deposited seeds of cucumber line APD147-5007Gy is ATCC Accession No. PTA-8624. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 4,822,949
U.S. Pat. No. 5,268,526
U.S. Pat. No. 5,349,128
U.S. Pat. No. 5,378,619
U.S. Pat. No. 5,463,175
U.S. Pat. No. 5,492,827
U.S. Pat. No. 5,500,365
U.S. Pat. No. 5,563,055
U.S. Pat. No. 5,623,066
U.S. Pat. No. 5,633,435
U.S. Pat. No. 5,689,052
U.S. Pat. No. 5,792,921
U.S. Pat. No. 5,880,275
U.S. Pat. No. 6,015,942
U.S. Pat. No. 6,084,152
U.S. Pat. No. 6,127,601
U.S. Pat. No. 6,194,638
U.S. Pat. No. 6,342,655
U.S. Pat. No. 6,765,130
U.S. Pat. No. 6,936,750
U.S. Pat. No. 7,041,875
U.S. Pat. No. 7,081,363
U.S. Pat. No. 7,098,378
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997 Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
PCT Appln. WO 99/31248
Potrykus et al., *Mol. Gen. Genet.*, 199:183-188, 1985.
Roshal et al., *EMBO J.*, 6:1155, 1987.
Sarreb et al., In: *Comparison of triploid and diploid cucumber in long-term liquid cultures*, Springer, 71(3):231-235, 2002.
Schaffner and Sheen, Plant Cell, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.

What is claimed is:

1. A seed of cucumber line APD147-5007Gy, a sample of seed of said line having been deposited under ATCC Accession Number PTA-8624.

2. A plant grown from the seed of claim 1.

3. A plant part of the plant of claim 2.

4. The plant part of claim 3, wherein said part is selected from the group consisting of a leaf, fruit, pollen, an ovule and a cell.

5. A tissue culture of regenerable cells of cucumber line APD147-5007Gy, a sample of seed of said line having been deposited under ATCC Accession Number PTA-8624.

6. The tissue culture according to claim 5, comprising cells or protoplasts from a plant part selected from the group consisting of embryos, meristems, cotyledons, pollen, leaves, anthers, roots, root tips, pistil, flower, seed and stalks.

7. A cucumber plant regenerated from the tissue culture of claim 6, wherein the regenerated plant expresses all of the physiological and morphological characteristics of cucumber line APD147-5007Gy, a sample of seed of said line having been deposited' under ATCC Accession Number PTA-8624.

8. A method of producing cucumber seed, comprising crossing the plant of claim 2 with itself or a second cucumber plant.

9. The method of claim 8, wherein the plant of cucumber line APD147-5007Gy is the female parent.

10. An F1 hybrid seed produced by the method of claim 8.

11. An F1 hybrid plant produced by growing the seed of claim 10.

12. A method for producing a seed of a line APD147-5007Gy-derived cucumber plant comprising the steps of:
(a) crossing a cucumber plant of line APD147-5007Gy, a sample of seed of said line having been deposited under ATCC Accession Number PTA-8624, with a second cucumber plant; and
(b) allowing seed of a APD147-5007Gy-derived cucumber plant to form.

13. The method of claim 12, further comprising the steps of:
(c) crossing a plant grown from said APD147-5007Gy-derived cucumber seed with itself or a second cucumber plant to yield additional APD147-5007Gy-derived cucumber seed;
(d) growing said additional APD147-5007Gy-derived cucumber seed of step (c) to yield additional APD147-5007Gy-derived cucumber plants; and
(e) repeating the crossing and growing steps of (c) and (d) to generate further APD147-5007Gy-derived cucumber plants.

14. A method of vegetatively propagating a plant of cucumber line APD147-5007Gy comprising the steps of:
(a) collecting tissue capable of being propagated from a plant of cucumber line APD147-5007Gy, a sample of seed of said line having been deposited under ATCC Accession Number PTA-8624;
(b) cultivating said tissue to obtain proliferated shoots; and
(c) rooting said proliferated shoots to obtain rooted plantlets.

15. The method of claim 14, further comprising growing plants from said rooted plantlets.

16. A method of introducing a desired trait into cucumber line APD147-5007Gy comprising:
(a) crossing a plant of line APD147-5007Gy, a sample of seed of said line having been deposited under ATCC Accession Number PTA-8624, with a second cucumber plant that comprises a desired trait to produce F1 progeny;
(b) selecting an F1 progeny that comprises the desired trait;
(c) crossing the selected F1 progeny with a plant of line APD147-5007Gy, a sample of seed of said line having been deposited under ATCC Accession Number PTA-8624, to produce backcross progeny;
(d) selecting backcross progeny comprising the desired trait and the physiological and morphological characteristic of cucumber line APD147-5007Gy; and
(e) repeating steps (c) and (d) three or more times in succession to produce selected fourth or higher backcross progeny that comprise the desired trait.

17. A cucumber plant produced by the method of claim 16.

18. A method of producing a plant of cucumber line APD147-5007Gy, a sample of seed of said line having been deposited under ATCC Accession Number PTA-8624, comprising an added desired trait, the method comprising introducing a transgene conferring the desired trait into a plant of cucumber line APD147-5007Gy.

19. A progeny of the plant of claim comprising the physiological and morphological characteristics of cucumber line APD147-5007Gy, a sample of seed of said line having been deposited under ATCC Accession Number PTA-8624.

20. A seed of the plant of claim 19.

21. A method of determining the genotype of the plant of claim 2, comprising obtaining a sample of nucleic acids from said plant and detecting in said nucleic acids a plurality of polymorphisms.

22. The method of claim 21, further comprising the step of storing the results of the step of detecting the plurality of polymorphisms on a computer readable medium.

23. A method of producing cucumbers comprising:
(a) obtaining the plant of claim 2, wherein the plant has been cultivated to maturity; and
(b) collecting cucumbers from the plant.

* * * * *